(12) United States Patent
Sakaguchi

(10) Patent No.: US 9,974,696 B2
(45) Date of Patent: May 22, 2018

(54) DISPOSABLE DIAPER

(71) Applicant: UNICHARM CORPORATION, Shikokuchuo-shi, Ehime (JP)

(72) Inventor: Satoru Sakaguchi, Kanoji (JP)

(73) Assignee: UNICHARM CORPORATION, Ehime (JP)

(*) Notice: Subject to any disclaimer, the term of this patent is extended or adjusted under 35 U.S.C. 154(b) by 404 days.

(21) Appl. No.: 14/431,773

(22) PCT Filed: Sep. 27, 2013

(86) PCT No.: PCT/JP2013/005767
§ 371 (c)(1),
(2) Date: Mar. 27, 2015

(87) PCT Pub. No.: WO2014/050137
PCT Pub. Date: Apr. 3, 2014

(65) Prior Publication Data
US 2015/0250657 A1    Sep. 10, 2015

(30) Foreign Application Priority Data

Sep. 28, 2012  (JP) ................ 2012-218716

(51) Int. Cl.
*A61F 13/15*  (2006.01)
*A61F 13/49*  (2006.01)
*A61F 13/494*  (2006.01)

(52) U.S. Cl.
CPC ...... *A61F 13/49007* (2013.01); *A61F 13/494* (2013.01); *A61F 13/49009* (2013.01);
(Continued)

(58) Field of Classification Search
CPC .......... A61F 13/49017; A61F 13/49009; A61F 13/48914; A61F 13/49007;
(Continued)

(56) References Cited

U.S. PATENT DOCUMENTS 5,662,636 A * 9/1997 Benjamin ......... A61F 13/49009
604/385.28

FOREIGN PATENT DOCUMENTS

JP    59-157301 A    9/1984
JP    10-211236 A    8/1998
(Continued)

OTHER PUBLICATIONS

International Search Report dated Jan. 7, 2014, corresponding International Application No. PCT/P2013/005767.
(Continued)

*Primary Examiner* — Jacqueline Stephens
(74) *Attorney, Agent, or Firm* — Hauptman Ham, LLP

(57) ABSTRACT

A disposable diaper (10) includes a pair of leg stretch units (75) extending along the leg opening (35) and can expand and contract in the product longitudinal direction.
A separation distance (D2) between the ends the leg stretch units (75) in the rear waistline region 30 is longer than the separation distance (D1) between the ends of the leg stretch units (75) in the front waistline region (20). The leg stretch units extending from the crotch region towards the rear waistline region are convex outwardly in the product widthwise direction. The leg stretch units extending from the crotch region towards the front waistline region are convex towards an inner side in the product widthwise direction.

9 Claims, 4 Drawing Sheets

(52) U.S. Cl.
CPC ... *A61F 13/49011* (2013.01); *A61F 13/49014* (2013.01); *A61F 13/49017* (2013.01); *A61F 2013/49039* (2013.01); *A61F 2013/49042* (2013.01); *A61F 2013/49046* (2013.01)

(58) Field of Classification Search
CPC ...... A61F 13/48911; A61F 2013/49039; A61F 13/49011; A61F 13/49014
USPC ............ 604/385.24, 385.25, 385.26, 385.27, 604/385.28, 385.3
See application file for complete search history.

(56) References Cited

FOREIGN PATENT DOCUMENTS

| | | |
|---|---|---|
| JP | 2005-7159 A | 1/2005 |
| JP | 2010-119463 A | 6/2010 |
| JP | 2010-279813 A | 12/2010 |
| WO | 2006/118214 A1 | 11/2006 |

OTHER PUBLICATIONS

Written Opinion dated Jan. 7, 2014, corresponding International Application No. PCT/JP2013/005767.
Office Action dated Feb. 19, 2013, corresponding to Japanese patent application No. 2012-218716.

\* cited by examiner

[Fig. 1]
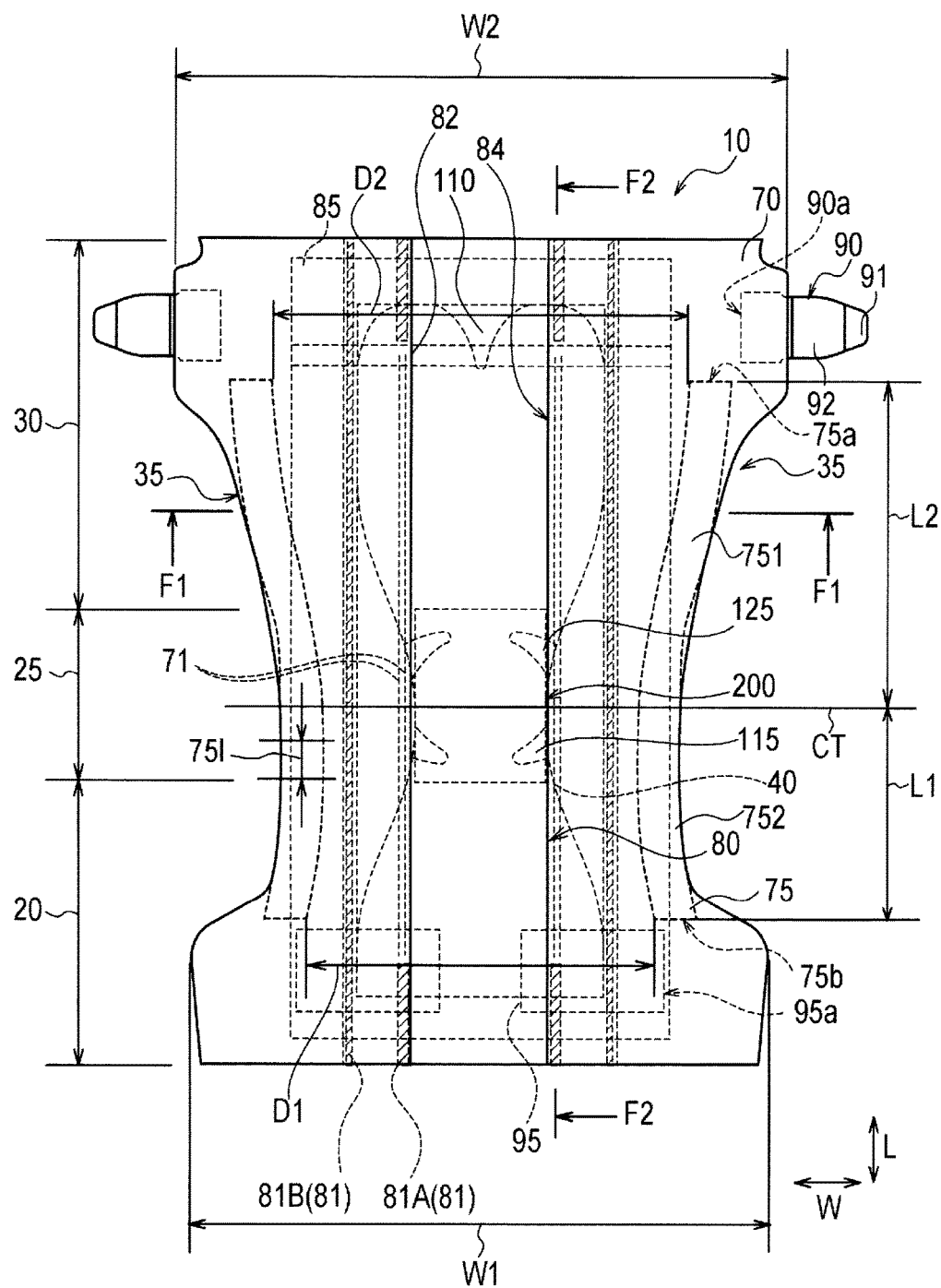

[Fig. 2]
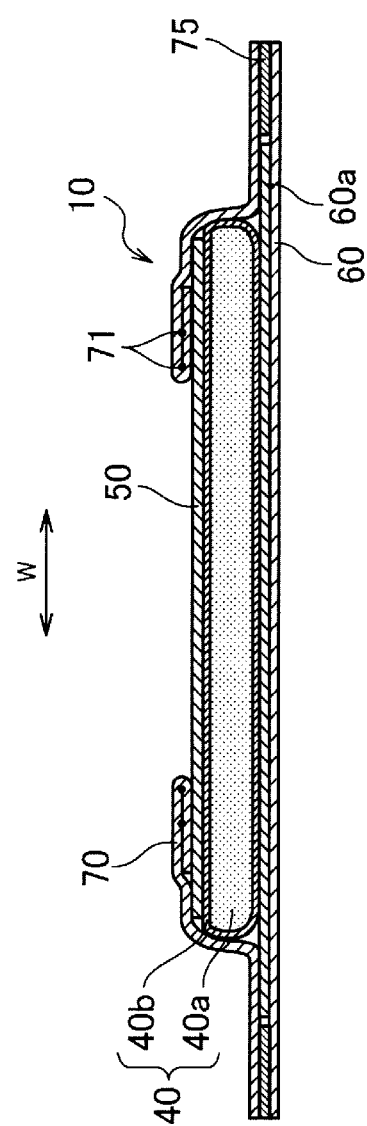

[Fig. 3]
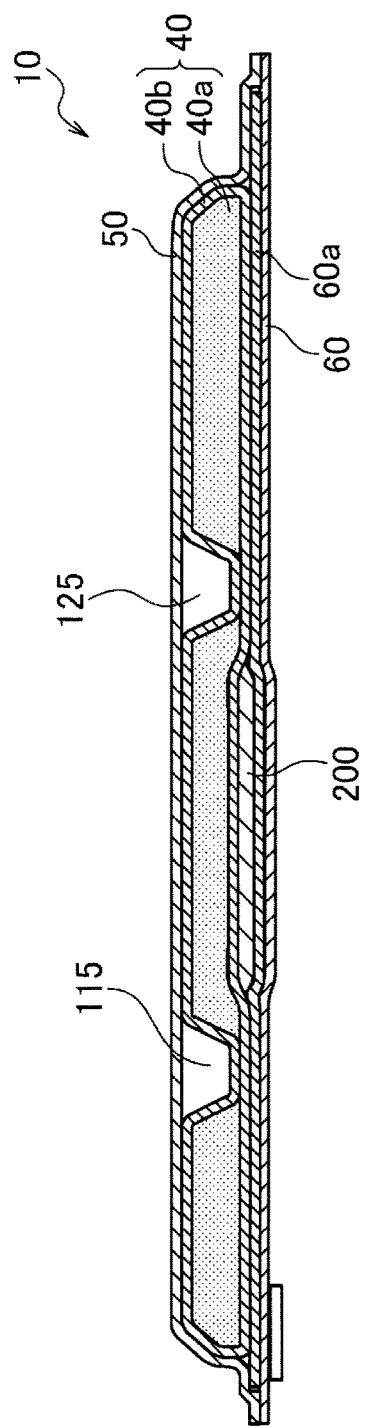

[Fig. 4]
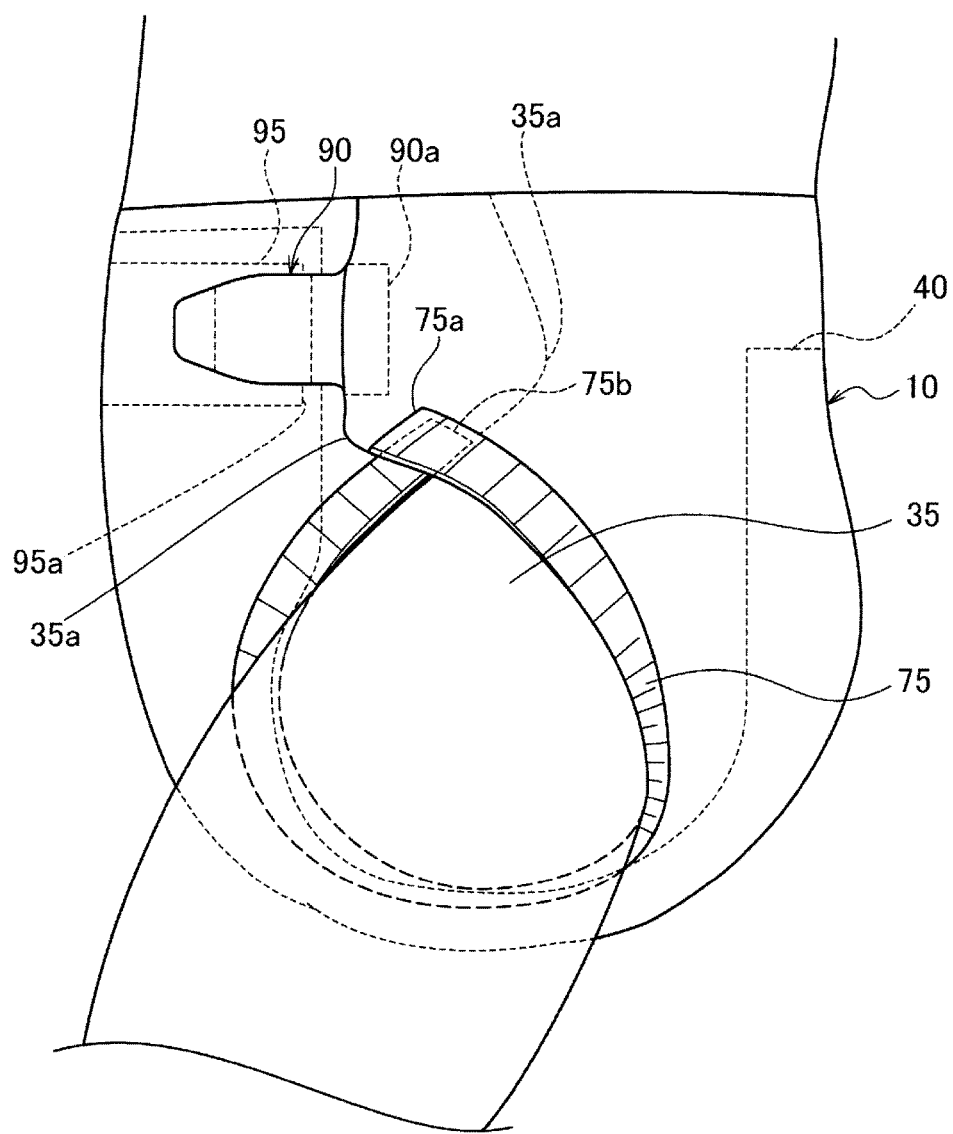

DISPOSABLE DIAPER

RELATED APPLICATIONS

The present application is a national phase of International Application Number PCT/JP2013/005767, filed Sep. 27, 2013, which claims priority to Japanese Application Number 2012-218716, filed Sep. 28, 2012.

TECHNICAL FIELD

The present disclosure relates to a disposable diaper including fastening tapes in a front waistline region.

BACKGROUND ART

As a disposable diaper mainly used for, e.g., infants and toddlers, a so-called open-type disposable diaper has been provided, in which fastening tapes for fixation are provided at side flaps in a rear waistline region.

The known structure for such an open-type disposable diaper in which the stiffness of the front ends of the fastening tapes is set smaller than that of the base ends of the fastening tapes (for example, Patent Literature 1, FIG. 1).

CITATION LIST

Patent Literature

[PTL 1] Japanese Unexamined Patent Application Publication No. 2005-7159

SUMMARY OF INVENTION

However, the inventor has recognized that the disposable diaper described above has the following problems. That is, when an infant or toddler wearing the disposable diaper makes a specific movement to move their body, the disposable diaper is more likely to shift downward. Specifically, when the infant or toddler takes a posture (a sitting posture) to bend their body due to the synergistic effect with their body type specific to an infant and toddler who has a prominent abdomen, the load is more likely to be applied to the front waistline region of the disposable diaper.

Specifically, the front waistline region of the disposable diaper, especially the fastening tapes having the greater stiffness than the other parts and target units having the fastening tapes attached thereinto are pressed by the abdomen of a wearer, so that the disposable diaper is more likely to shift downward of their body.

Therefore, the present invention has been achieved in view of the above-described situation, and an object thereof is to provide a disposable diaper that is less likely to shift even when a wearer (an infant and toddler) takes a posture to bend their body.

In some embodiments, a disposable diaper comprises: a front waistline region, a rear waistline region, a crotch region, a product longitudinal direction from the front waistline region towards the rear waistline region, a product widthwise direction that is perpendicular to the product longitudinal direction, an absorber including an absorbent core with a liquid retention property, and a pair of side flaps provided at side edges of the absorber in the product widthwise direction. A fastening tape is provided to each of the side flap, projects from the rear waistline region outwardly in the product widthwise direction, and is configured to be attached to a target unit formed in the front waistline region. A pair of leg openings is provided in the side flaps, and concave inwardly in the product widthwise direction. A pair of leg stretch units is expansible and contractible along the leg openings.

Each of the leg stretch units has a part bending outwardly in the product widthwise direction as the leg stretch unit extends from the crotch region outwardly in the product longitudinal direction. A separation distance between the leg stretch units in the product widthwise direction in the crotch region is smaller than separation distances between the leg stretch units in the product widthwise direction in the front waistline region and the rear waistline region. The separation distance in the rear waistline region is longer than the separation distance in the front waistline region. The leg stretch units extending from the crotch region towards the rear waistline region are convex outwardly in the product widthwise direction. The leg stretch units extending from the crotch region towards the front waistline region are convex inwardly in the product widthwise direction.

That is, the leg stretch units have a curved shape along the leg openings wherein, from the crotch region, in the direction of the front waistline region, the leg stretch units curve inwardly towards the inner side in the product widthwise direction (are convex towards the widthwise centre of the diaper); from the crotch region, in the direction of the rear waistline region, the leg stretch units curve outwardly towards the outer side in the product widthwise direction (are convex towards the widthwise outer side of the diaper); the distance in the product widthwise direction between the inner edges of the leg stretch units is smaller in the crotch region than in both of the front and rear waist regions; and the distance in the product widthwise direction between the inner edges of the leg stretch units is larger in the rear waist region than in the front waist region.

BRIEF DESCRIPTION OF DRAWINGS

FIG. 1 is a plan view of a disposable diaper according to at least one embodiment.

FIG. 2 is a cross-sectional view of the disposable diaper along an F1-F1 line shown in FIG. 1.

FIG. 3 is a cross-sectional view of the disposable diaper along an F2-F2 line shown in FIG. 1.

FIG. 4 is a diagram illustrating a state in which the disposable diaper according to at least one embodiment is worn by a wearer.

DESCRIPTION OF EMBODIMENTS

Hereinafter, at least one embodiment of a disposable diaper according to the present invention is described with reference to accompanying drawings. In the following description of the drawings, the same or similar reference numerals are used to designate the same or similar portions. It will be appreciated that the drawings are schematically shown and the ratio and the like of each dimension might be different from the real products.

Accordingly, specific dimensions should be determined in consideration of the explanation below. Moreover, among the drawings, the respective dimensional relations or ratios may differ.

(1) Overall Schematic Configuration of Disposable Diaper

FIG. 1 is a plan view of a disposable diaper 10 according to at least one embodiment. FIG. 2 is a cross-sectional view of the disposable diaper 10 along an F1-F1 line shown in FIG. 1. FIG. 3 is a cross-sectional view of the disposable diaper 10 along an F2-F2 line shown in FIG. 1. It should be noted that the plan view of FIG. 1 is a diagram in which leg stretch unit 75 and leg side gathers 80 are in an expanded state such that wrinkles are not formed in a topsheet 50 and side flaps 70, for example, that configure the disposable diaper 10.

The disposable diaper 10 includes a front waistline region 20, a crotch region 25, and a rear waistline region 30. The front waistline region 20 is a portion that is in contact with the front waistline (ventral portion) of the wearer. Furthermore, the rear waistline region 30 is a portion that is in contact with the rear waistline (dorsal portion) of the wearer. The crotch region 25 is positioned between the front waistline region 20 and the rear waistline region 30.

Furthermore, a pair of leg openings 35 are formed in the disposable diaper 10. The leg openings 35, which are provided at the side ends in the product widthwise direction of the disposable diaper, are the portions that are arranged to fit around the legs of the wearer when the disposable diaper is worn by the wearer.

In at least one embodiment, the direction from the front waistline region 20 to the rear waistline region 30 is called a product longitudinal direction L, and the direction perpendicular to the product longitudinal direction L is called a product widthwise direction W.

The disposable diaper 10 includes an absorber 40 running across the crotch region 25 and extending from the crotch region towards at least one of the front waistline region 20 and the rear waistline region 30. The absorber 40 is configured by an absorbent core 40a with a liquid retention property and a core wrap 40b.

The absorbent core 40a can be configured appropriately by using components and materials, such as ground pulp and high absorbent polymer. The absorbent core 40a is wrapped by the sheet-like core wrap 40b.

The core wrap 40b is a sheet for covering the absorbent core 40a. Apart of at least the skin surface side of the core wrap 40b is configured by various nonwoven fabrics having permeability or by a tissue sheet. For example, an air-through nonwoven fabric, a spunbond nonwoven fabric, or an SMS (spunbond-meltblown-spunbond) nonwoven fabric having a mass of approximately 10 to 30 g/m$^2$, or a tissue sheet having a mass of approximately 10 to 30 g/ms may be used.

Furthermore, the absorbent core 40a positioned in the crotch region 25 has a narrow part having a width in the product widthwise direction W smaller than that of the absorbent core 40a positioned in the front waistline region 20 and the rear waistline region 30. Specifically, a part of the absorbent core 40a provided with a crotch stretch unit 200 to be described later corresponds to the narrow part.

On the top side (skin contact surface side) of the absorber 40 is provided a liquid-permeable topsheet 50. Furthermore, on the back side (non-skin contact surface side) of the absorber 40 is provided a liquid-impermeable backsheet 60a.

A side flap 70 is provided an each side edge in the product widthwise direction W of the absorber 40. The side flaps 70 are made of one or two or more pieces of nonwoven fabrics overlapping one another. Specifically, in the side flap 70, the leg opening 35 which is convex inwardly in the product widthwise direction W of the absorber 40 is formed.

Furthermore, a fastening tape 90 is provided in each of the pair of side flaps 70.

The fastening tapes 90 are positioned in the rear waistline region 30 and extend in the product widthwise direction W in the rear waistline region 30, and hold the disposable diaper 10 onto the body of the wearer by being secured to target units 95 of the front waistline region.

The fastening tapes 90 extend from the rear waistline region 30 to both outer sides in the product widthwise direction W.

The target units 95 are formed at the non-skin contact surface within the front waistline region 20 and are configured so that the pair of fastening tapes 90 is attached thereto, respectively.

In at least one embodiment, a waistline retaining unit is made up of the front waistline region 20, the rear waistline region 30, and the fastening tapes 90. The waistline retaining unit in the rear waistline region 30 corresponds to a range extending in the widthwise direction from a region provided with engaging members of the fastening tapes 90. The waistline retaining unit in the front waistline region 20 corresponds to a range extending in the widthwise direction from a region provided with the target units 95.

Furthermore, the disposable diaper 10 includes a crotch stretch unit 200 formed in a region overlapping the absorber 40 in the crotch region 25. The configuration of the crotch stretch unit 200 is described later in detail.

The top side (topsheet 50 side) of the absorber 40 includes a pair of leg stretch units 75 formed around the leg openings 35. The pair of leg stretch units 7 can expand and contract (i.e., is expansible and contractible) in the product longitudinal direction L.

The leg stretch units 75 extend along the leg opening 35 in the product longitudinal direction L. Furthermore, the leg stretch units 75 are partially stretchable at least in the product longitudinal direction L.

The leg stretch units 75 are configured to be longer than the crotch stretch unit 200 in the product longitudinal direction L, and are provided at the outer side from the crotch stretch unit 200 in the product widthwise direction W.

It is sufficient that the leg stretch units 75 are configured such that the leg openings 35 are stretchable in the product longitudinal direction. For this purpose, the leg stretch units may be arranged along the leg openings 35, or a part of the leg stretch units may be arranged in an inclined state with respect to the leg openings 35. That is, the leg stretch units 75 are stretchable in the product longitudinal direction and may be arranged along the leg openings 35, or partly at an angle to the leg openings 35.

Furthermore, the leg stretch units 75 correspond to the portion that is substantially contracted in the product longitudinal direction by a stretchable sheet or the like, and can be conceived as the portion exclusive of the portion in which the stretchable sheet is arranged in a state in which the contractile force is not exhibited. The configuration of the leg stretch units 75 is described later in detail.

<Leg Side Gathers>

Additionally, a pair of leg side gathers 80 extending along the product lengthwise direction L are provided in the inner side of the pair of leg stretch units 75 (closer to the center in the product widthwise direction W). The leg side gathers 80, which are provided in the inner ends in the product widthwise direction of the side flaps, are upright stretchable gathers arranged in the product widthwise direction between the leg stretch units. That is, a pair of leg side gathers are provided on the side flaps 70, at the inner edges (in the longitudinal direction) of said side flaps 70, and are thus positioned towards the inner side of the diaper (in the product widthwise direction) to the leg stretch units 75.

The leg side gathers 80 are arranged in the product widthwise direction between the leg stretch units 75. The leg side gathers 80 may be made from a sheet member which is different from that of the side flap 70.

The side flaps 70 are folded back to the side of the topsheet in the inner ends in the product widthwise direction and are formed by laminating the two layers formed by the fold. That is, each side flap has a folded end portion at the inner side thereof wherein the outer edge thereof is folded under to form a double layer.

The width W1 of the side flap 70 in the front waistline region 20 is smaller than the width of the side flap 70 in the rear waistline region 30. Furthermore, an elastic member 71 (see FIG. 2) in a state of being stretched out in the product longitudinal direction, is provided between the two layers of side flap 70 in the folded portion. These side flaps 70 and elastic members 71 form the leg side gathers 80.

Each of the leg side gathers 80 has a joining portion 81 to be joined to the topsheet 50 or the backsheet 60*a*, and a free end portion 82 having an elastic member arranged therein. A center part of the free end portion 82 in the longitudinal direction is contracted in the product longitudinal direction by means of the elastic member 71 and configures a contracting unit 84. A center part of the free end portion 82 is positioned in the crotch region. When the disposable diaper is worn, each of the leg side gathers 80 rises up with the joining portion 81 as the base end, and the contracting unit 84 of the free end portion 82, as the top, comes in contact with the skin of a wearer. That is, the Joining portion serves as the base end for a leg side stretch unit to rise up.

It is to be noted that the contracting unit 84 is a part that is practically contracted in the product longitudinal direction by means of the elastic member 71, except for a part in which the elastic member 71 is arranged with no contraction force exerted. Furthermore, the joining portion 81 in which the side flap 70 and the topsheet 50 (or the backsheet 60*a* or the like) are bonded together in the leg side gathers are marked with diagonal lines and shown in FIG. 1.

A plurality of joining portions 81 are provided, in which first joining portions 81A are arranged on the outer side in the product longitudinal direction of the contracting unit 84, while second joining portions 81B are arranged on the outer side in the product widthwise direction of the contracting unit 84. Therefore, each of the leg side gathers 80 is configured so that the center part including the crotch region 25 in the product longitudinal direction rises up towards a wearer's side.

Of the joining portions 81 of the leg side gathers 80, the first joining portion 81A arranged on the outer side in the product longitudinal direction of the contracting unit 84 is joined to the topsheet 50.

Of the joining portions 81 of the leg side gathers 80, the second joining portion 81B arranged on the outer side in the product widthwise direction of the contracting unit 84 is arranged between a crotch stretch unit 200 and the leg stretch unit 75 in the product widthwise direction W. The full length in the product longitudinal direction of the second joining portion 81B is joined to the backsheet 60*a* (and partially to the exterior sheet 60). Accordingly, the leg stretch units 75 extend along the legs of wearer and the crotch stretch unit 200 extends along the crotch of a wearer, respectively. That is, a supporting point for the leg side gathers 80 to rise up is arranged between the leg stretch units and crotch stretch unit so that the leg side gathers 80 rise up towards the wearer while maintaining the height of the leg side gathers 80 without getting caught between the wearer's body and these stretch unit, thereby making it possible to provide a more reliable function of leakage prevention.

Various types of configurations can be adopted for the joining portion 81 of the leg side gathers 80. The joining portion, for example, is configured to be an upright proximal end, and could be a portion extending from the crotch portion to the front waistline region and the rear waistline region in the product longitudinal direction and joined with the topsheet, or a portion joined with the liquid-impermeable backsheet and the exterior sheet in the outer side in the widthwise direction from the absorbent core 40*a*.

Furthermore, the leg side gathers are not limited to the above configuration as long as the leg side gathers are upright gathers arranged, in the product widthwise direction, between the leg stretch units, and any configuration of the leg side gathers can surely be adopted.

<Waistline Stretch Unit>

A waistline stretch unit 85 that can expand and contract in the product widthwise direction is provided between the pair of fastening tapes in the product widthwise direction. The waistline stretch unit 85 expands and contract in the widthwise direction between the fastening tapes.

In at least one embodiment, the waistline stretch unit 85 is made from a stretch sheet. A member configuring the waistline stretch unit 85 is not particularly limited but it is preferable to use something as thin as possible, which has a low bending stiffness and a small reduction in width. By configuring the waistline stretch unit 85 from a member having a low bending stiffness, the waistline stretch unit 85 can be easily bent along the body, thereby being able to fit along the body without putting the load on the body of a wearer. Furthermore, by making the waistline stretch unit 85 from a member having a small reduction in width, the disposable diaper can be prevented from contracting in the product longitudinal in a case of the disposable diaper being stretched out in the product widthwise direction, so that the disposable diaper can be prevented from hanging down towards the crotch side within the waistline of the wearer.

In at least one embodiment, as the waistline stretch unit 85, an extendable film of 20 to 45 $g/m^2$ in base weight was employed.

After being extended up to 1.5 to 2.5 times its length in the non-expanded state (natural state), the waistline stretch unit 85 is adhered onto the exterior sheet 60 with a hot-melt adhesive or by heat processing.

In at least one embodiment, the waistline stretch unit 85 is arranged between the exterior sheet 60 and the backsheet 60*a* (see FIG. 1). However, if the core wrap 40*b* is configured to extend in the outer side in the product longitudinal direction from the absorbent core 40*a*, the waistline stretch unit 85 may be arranged between the core wrap 40*b* and the backsheet 60*a* or exterior sheet 60. The position of the waistline stretch unit is not particularly restricted. Furthermore, in a region in which the absorber is not arranged, the waistline stretch unit may be arranged between the side flaps 70 and the backsheet 60*a* or exterior sheet 60.

The waistline stretch unit according to at least one embodiment is configured to stretch in the product widthwise direction: however, the waistline stretch unit may be configured to stretch in the product widthwise direction and in the product longitudinal direction.

<Notch 110>

In the absorber 40 of the rear waistline region, a notch 110 is provided as a low rigidity region that either has a basis weight lower than the other parts of the absorber, or in which the absorbent core 40*a* does not exist. The notch 110 has a length in the product widthwise direction that shortens gradually from the end at the side of the rear waistline region of the absorber 40 towards the side of the crotch region. That is, the notch tapers from its end nearest the outer side of the diaper in the product longitudinal direction, to its end nearest the inner side of the diaper in the product longitudinal direction. More specifically, the notch 110 has a wedge shape in the plan view of the disposable diaper. Furthermore, the boundary between the absorbent core 40*a* and the notch 110 is formed in the shape of an arc such as a shape convex inwardly in the product widthwise direction W. The absorber 40 at the outer side in the product widthwise direction from the notch 110 has a trapezoidal shape such as a convex shape towards the end of the side of the rear waistline region.

A part of the notch 110 is arranged to be overlapping the waistline stretch unit 85 in the plan view of the disposable diaper. In at least one embodiment, the waistline stretch unit 85 is arranged to be overlapping a part of the notch 110; however, the entire notch 110 may be arranged to be overlapping waistline stretch unit 85.

By forming such a notch 110, without obstructing the stretching of the waistline stretch unit 85, even when the waistline stretch unit 85 contracts, the notch 110 narrows and the space between the respective sides of the absorber at both sides in the product widthwise direction from the notch 110 also narrows, because of which it becomes difficult for the absorber 40 to rise in the unintended shape. In view of preventing the leakage of the excretions, the notch 110 is preferably narrower than the width of the waistline stretch unit 85.

Furthermore, if the absorber 40 is contracted in the product widthwise direction W by the waistline stretch unit 85 and the space between each side of the absorber in the product widthwise direction from the notch 110 also narrows, the part towards the end of the side of the rear waistline region 30 of the notch 110 shifts more inwardly in the product widthwise direction W than the part towards the crotch region 25, and therefore, a difference in the amount of contraction in the product widthwise direction W occurs between the part at the side of the rear waistline region 30 and the part towards the crotch region 25, because of which the rear waistline region 30 rises.

That is, because the waistline stretch unit 85 that can expand and contract in the product widthwise direction W and the wedge-shaped notch 110 are present, the disposable diaper 10 easily swells at the non-skin surface side resulting in a cup shape, when the disposable diaper 10 is worn. Owing to the fact that the disposable diaper is formed in the aforementioned cup shape, a part of the disposable diaper forms not a plane surface but a three-dimensional shape, thereby making it easy to run along the roundness of the body of the wearer.

Furthermore, in at least one embodiment, where the absorbent core 40*a* does not exist in the notch 110, and the waistline stretch unit 85 exists so as to overlap the notch 110, the part towards the end of the side of the rear waistline region 30 in the product longitudinal direction L shifts more inwardly in the product widthwise direction W than the position of the end of the absorbent core 40*a* because of which the rise of the rear waistline region 30 becomes more remarkable, and the above-mentioned cup shape can be formed in a more stable manner.

In at least one embodiment, because the waistline stretch unit 85 exists beyond the side edges in the product widthwise direction W of the absorbent core 40*a*, the disposable diaper 10 can be formed in the shape of a cup, and the absorbent core 40*a* positioned towards the end of the side of the rear waistline region 30 in the product longitudinal direction L can actively run along the body of the wearer. Furthermore, because at least a part of the waistline stretch unit 85 and the low rigidity region exists in a tape arrangement region A1 provided with a pair of fastening tapes 90, even when the disposable diaper 10 is fitted to a wearer by opening out the disposable diaper 10 and then making the wearer lie down on the disposable diaper, the waistline stretch unit 85 that exists beyond the side edges in the product widthwise direction W of the absorbent core 40*a* is not placed under the body of the wearer, and as a result, by pulling the fastening tapes 90, the side edges of the waistline stretch unit 85 expand, and the disposable diaper can be more surely made to run the cup-shaped position towards the waist along the body of the wearer.

In at least one embodiment, the absorbent core 40*a* at the outer side in the product widthwise direction from the notch 110 has a convex shape towards the side of the rear waistline region. Therefore, in addition to the above-mentioned fact that a cup shape in which the disposable diaper 10 swells at the non-skin surface side can be formed easily, the surface area of the absorbent core 40*a* is maintained, enabling the prevention of leakage of excretions from the ends of the absorbent core 40*a*.

In at least one embodiment, the notch 110 is wedge shaped, and the boundary between the absorbent core 40*a* and the notch 110 is in the shape of an arch such as a convex shape towards the crotch region 25. The radius of the arc is between 50 mm and 200 mm. Therefore, the width in the product widthwise direction W of the notch 110 increases non-linearly towards the end of the side of the rear waistline region 30 in the product longitudinal direction L, because of which the rise of the rear waistline region 30 becomes more remarkable, and the cup shape can easily be formed in a more stable manner. Additionally, because the boundary between the absorbent core 40*a* and the notch 110 is formed in the shape of an arc such as a convex shape towards the crotch region 25, due to the contraction of the notch 110, the rear waistline region 30 takes a curved cup shape, which can easily run along the curved hips of the wearer.

Furthermore, due to the formation of the notch 110, a convex shape towards the side of the rear waistline region is formed on both left and right at the end of the side of the rear waistline region of the absorber 40. The shape of the absorber references the placing of the hips, and is effective in more easily enabling the user to set the diaper at the correct position for the wearer.

The bending rigidity in at least one embodiment is based on the rigidity value conforming to the Taber method (JISP8125), and can also be checked by measuring as described below. First of all, with the disposable diaper in the developed state, a sample of the portion where the bending rigidity is to be measured (for example, the absorber) is extracted. As regards the sample, the length of the sample in the widthwise direction is 70 mm; the length of the sample in the product longitudinal direction is 38 mm . . . . If a stretchable elastic member is included in the sample, the elastic member is removed. The Taber Stiffness Tester manufactured by Yasuda Seiki Seisakusho Ltd. is used for measuring the rigidity value. Ten samples are taken and measurement is performed for each sample, and the average value is set as the rigidity value.

The measurement procedure is as described in (a) through (e) below.
  (a) Measure the thickness (A) of the extracted samples.
  (b) Next, insert the sample such that the sample is in contact with the center of the chuck (lower) of the Tester.

(c) Adjust the total left-right interval between the support roller and the sample to (A) (the thickness value)×0.80 (mm).

(d) Appropriately select an auxiliary weight such that the specified load scale is in the range of 15 to 85% of the maximum scale.

(e) Rotate the samples in both left and right directions, stop at the point where the 15' support marked line and the central marking of the pendulum match, and read the value on the tester. Consider the value on the left side of the scale as (B) and the value on the right side of the scale as (C).

The rigidity value is calculated by the below formula:

$$\text{Rigidity value (mN·m)} = (((B)+(C))/2) \text{ times (Auxiliary weight coefficient) times } 9.81 \text{ times } 10^{-2} \quad \text{Formula}$$

If a width of 38 mm cannot be acquired for the specimen, perform conversion to the bending moment of 38-mm width.

The conversion to the bending moment of 38-mm width can be performed by multiplying the measurement result by 38/d on the condition that a sample width is dmm.

It is to be noted that a thickness was measured using a dial thickness gauge, PEACOCK, manufactured by OZAKI MFG. CO., LTD., while adjustment was made so as to have a load of 6.0 gf/cm$^2$ with a measuring terminal in a circle having a diameter of 10 mm.

The higher the rigidity value thus measured, the higher the bending rigidity, and the lower the rigidity value, the lower the bending rigidity.

<Configuration of Fastening Tape and Target Unit>

As shown in FIG. 1, the fastening tape 90 is installed in the region of the side flaps 70 corresponding to the rear waistline region 30. The fastening tape 90 includes a base sheet 91 connected with the side flaps 70, and a hook sheet 92 provided with a plurality of engagement hooks (not shown in the figure), and fixed onto the base sheet 91. The hook sheet 92 is a region provided with the engaging member and the aforementioned waistline retaining unit is a region extending in the widthwise direction from the hook sheet 92.

The hook sheet 92 is fixed, specifically, joined with the base sheet 91. The hook sheet 92 and the base sheet 91 are preferably joined such that the rigidity of the fastening tape 90 does not become more than necessary. Specifically, the hook sheet 92 and the base sheet 91 are preferably joined by a hot-melt adhesive applied intermittently in dot shape, line shape, or spiral shape. The hook sheet 92 and the base sheet 91 may also be joined with a heat seal, for example.

The base sheet 91 is configured by one layer of nonwoven fabrics or two or more plurality of layers of nonwoven fabrics overlapping one another. A nonwoven fabric manufactured by a manufacturing method such as spun bond (SB) or spun bond-melt blown-spun bond (SMS) can be used as the base sheet 91. The basis weight of the nonwoven fabric (or total basis weight in the case of a plurality of layers) configuring the base sheet 91 is preferably 30 to 120 g/m, and more preferably 40 to 90 g/m$^2$.

Furthermore, it is preferable that a value of the bending stiffness per unit length in the product longitudinal direction L and the product widthwise direction W of the fastening tape 90 be 3.0 gf·cm$^2$/cm or less, more preferably 2.5 gf·cm$^2$/cm or less. Yet further, from the viewpoint of ensuring the strength required for the fastening tape 90, it is preferable that this value of the bending stiffness be 0.5 gf·cm$^2$/cm or less. It is to be noted that a value of the bending stiffness of the fastening tape 90 may be controlled by adjusting weight per area or the number of piles of nonwoven clothes mainly constituting the base sheet 91.

The bending property of the fastening tape was measured using KES bending tester manufactured by KATO TECH Co., Ltd. Specifically, B value (bending stiffness) was measured.

Specifically, a KES method is described in detail in "the standardization and analysis of hand evaluation" Vol. 2 (issued on Jul. 10, 1980, Hand Evaluation and Standardization Committee, the Textile Machinery Society of Japan). Thus, a measurement method of each mechanical property is described only for measurement conditions related to the present measurement.

The bending property was measured using KES-FB2 manufactured by KATO TECH Co., Ltd. by attached each sample between chucks (the skin surface side (the inner side) of the fastening tape in the diaper is set as a downward direction), bending the sample to the front side up to maximum curvature +2.5 cm-1, bending the sample to the back side up to maximum curvature −2.5 cm-1, and returning the sample to the original position.

Having such a flexible bending property value, the fastening tape 90 follows the body shapes well, thereby making it possible to prevent effectively the disposable diaper 10 from shifting from the abdominal side. That is, owing to the synergistic effect with the fact that the leg stretch units 75 prevent the legs from shifting from the crotch of the disposable diaper 10, the shifting of the disposable diaper 10 can be prevented more effectively.

The target unit 95 is provided at the non-skin contact surface side of the exterior sheet 60 of the front waistline region. The target unit 95, which is configured such that the engagement hooks of the fastening tape are engaged therein, functions as the loop in a hook-and-loop fastening system. An air-through nonwoven fabric, for example, can be used as the target unit.

A fibrous nonwoven fabric prepared from polyolefin-based thermoplastic synthetic resin fibers, or a polyolefin-based thermoplastic synthetic resin film, for example, can be used for the target unit 95. Furthermore, the loop provided in the target unit can be formed by a polyolefin-based thermoplastic synthetic resin.

In addition, a bulky nonwoven fabric, which is embossed partially to prevent fluffing on the surface of the nonwoven fabric may be used as the target unit 95.

Furthermore, the target unit may also be formed by providing the exterior sheet 60 of the disposable diaper with a nonwoven fabric, and then printing a design showing the position of attaching the fastening tape 90 on the non-skin contact surface side of the exterior sheet 60, or by arranging the sheet with a design on the non-skin contact surface side of the exterior sheet 60.

(2) Leg Stretch Unit

The leg stretch units 75 are arranged along the leg openings 35 provided on the outer side in the product widthwise direction of the absorber 40 and are configured so as to be stretchable in the product longitudinal direction L. Each of the leg stretch units 75 has a widthwise inner end region 751 which defines the innermost portion of the leg stretch unit 75 in the product widthwise direction and is placed in the crotch region. That is, in each leg stretch unit 75 the innermost part 751, i.e., the part closest to the centre of the diaper in the product widthwise direction, is located in the crotch region 25. The leg openings 35 and the leg stretch units 75 extend outwardly in the product widthwise direction especially in the rear waistline region as the leg openings 35 and the leg stretch units 75 extend from the crotch region 25 outwardly in the product longitudinal direction. It is to be noted that the widthwise inner end region 751 of the leg stretch unit 75 may be arranged in a continuous manner in the product longitudinal direction or may be arranged in non-continuous manner in the product longitudinal direction. In at least one embodiment, the innermost region in the widthwise direction of the leg opening 35 is placed in the crotch region and corresponds to the widthwise inner end region 751 of the leg stretch unit 75. In at least another embodiment, the innermost region in the widthwise direction of the leg opening 35 may not necessarily correspond to the widthwise inner end region 751 of the leg stretch unit 75.

The leg stretch units 75 of at least one embodiment are configured by a stretchable sheet. For example, a stretch film formed by melting a thermoplastic elastomer resin, such as urethane and styrene, and then converting into the shape of a film, a stretchable nonwoven fabric formed from stretchable fibers, or a composite sheet formed by pasting together inextensible sheets that have been partially cut into a stretch film and stretchable nonwoven fabric, or have been made fragile may be used as the stretchable sheet.

Furthermore, instead of the stretchable sheet, a single or a plurality of thread-like or band-like elastic members made of polyurethane elastic fibers and natural rubber may be arranged to configure the leg stretch units 75.

Each of the leg stretch units 75 is configured so that one end 75a in the product longitudinal direction L of the leg stretch unit 75 and the other end 75b in the product longitudinal direction L of the leg stretch unit 75 are superimposed in a state where the fastening tape 90 is attached to a predetermined position of the target unit 95 (see FIG. 4). It is to be noted that the predetermined position of the target unit 95 means each of attaching positions at which the fastening tapes 90 are attached to the target units 95, respectively, in a state where the pair of fastening tapes 90 are in adjacent contact with each other. With such an attaching position set as a reference point, the disposable diaper 10 can fit suitably onto a wearer with a small body shape (such as an infant or toddler), who is most likely to cause the shifting or space from their body. Furthermore, as long as the disposable diaper 10 can fit suitably onto such a wearer with a small body shape, it also can fit suitably onto a wearer with a large body shape by use of a size (waistline) adjustment function as the merit of a tape-type disposable diaper.

Furthermore, in a state where the fastening tape 90 is attached to the predetermined position of the target unit 95, a region of the side flap 70 having the presence of the fastening tape 90, the leg stretch unit 75, and the target unit 95 are arranged separately from each other. In other words, in a state where the fastening tape 90 is attached to the predetermined position of the target unit 95, a region of the side flap 70 having the presence of the fastening tape 90, the leg stretch unit 75, and the target unit 95 do not overlap. It is to be noted that the region of the side flap 70 having the presence of the fastening tape 90 means a region in which the side flap 70 and the base sheet 91 are superimposed (see FIG. 1). It is to be noted that FIG. 4 shows not a state where the target unit 95 is locked to a predetermined position but an example of a state where the disposable diaper according to the present invention is worn.

The leg stretch unit 75 may be arranged between the side flap 70 and the exterior sheet 60. Alternatively, in a region provided with the backsheet 60a arranged between the absorber 40 and the exterior sheet 60, the leg stretch unit 75 may be arranged between the backsheet 60a and the side flap 70.

It is preferred that the stretchable sheet configuring the leg stretch units 75 has, at least in the crotch region 25, a width of 5 mm (width in the product widthwise direction W in the natural state of the disposable diaper 10) or more and 45 mm or less, and more preferably 12.5 mm or more and 35 mm or less. When the width is less than 5 mm, the effect of lowering of the load on the skin by the elastic elements achieved by substantially running, in the form of a surface of the leg stretch units, along the area around the legs of the wearer so as to prevent the partial concentration of the securing force is less likely exhibited. When the width exceeds 45 mm, the region along the area around the legs becomes too wide in comparison to the length in the product widthwise direction of the entire disposable diaper, and as a result, the stretchable sheet might become entangled at the side of the wearer's body, or may turn over.

Meanwhile, the dimension described above was measured by placing a measuring tape (tape: glass fiber contained polyvinyl chloride coating) manufactured by Shinwa Rules Co., Ltd., along a measurement target area. Specifically 10 samples were measured in dimension and the dimension described above was determined based on the average value.

The ratio of expansion and contraction of the leg stretch units 75 is preferably 1.5 times to 2.2 times. In at least one embodiment, the ratio of expansion and contraction of the leg stretch units 75 is set to 1.8 to 2.0 times. The ratio of expansion and contraction of the leg stretch units 75 is measured as described below.

The ratio of expansion and contraction of the leg stretch units 75 implies the extent of the expansion and contraction of the leg stretch units 75, and is stipulated as below:

> The ratio of expansion and contraction of the leg stretch units 75=(Length of the leg stretch units 75 in the expanded state)/(Length of the leg stretch units 75 in the natural state)

The ratio of expansion and contraction of the leg stretch units 75 is measured as described below.

Firstly, if the disposable diaper 10 is inserted in a package, for example, then the disposable diaper 10 is taken out of the package. Next, the arrangement region of the leg stretch unit 75 is cut out.

At this time, cutting is performed by including the exterior sheet joined with the leg stretch unit 75. The ratio of expansion and contraction of the sample including the leg stretch unit after cutting is measured and the ratio of expansion and contraction of the leg stretch unit is calculated.

Each sample is kept for 60 minutes under an atmosphere having a temperature of 20° C.±2° C., and a relative humidity of 60% RH±5% RH, and the length of the leg stretch unit is measured along the stretching direction. This length is the "Length of the leg stretch unit in the natural state".

Secondly, the length in the stretching direction of the desired region of the disposable diaper in this state (that is, in the natural state), and the length in the stretching direction of the desired region, when the disposable diaper is extended from its natural state until wrinkles caused by the elastic members are not visible on the non-stretchable sheet, are measured. This length is the "Length of the leg stretch unit in the expanded state".

The ratio of expansion and contraction is measured by using these measurement results and calculating according to the formulae described above.

Furthermore, the interval (a separation distance D) between the inner ends of the pair of the left-right leg stretch units 75 in the product widthwise direction W widens from the crotch region 25 towards the front waistline region 20, and also widens from the crotch region 25 towards the rear waistline region 30.

That is, of the pair of leg stretch units 75, a separation distance D in the product widthwise direction W between the leg stretch units 75 becomes longer as the leg stretch units extend outwardly in the product longitudinal direction L. Furthermore, each of the leg stretch units 75 has a part 75w bending outwardly in the product widthwise direction W as the leg stretch unit extends from the crotch region 25 outwardly in the product longitudinal direction L.

When the diaper is worn on the body of the wearer, if the leg stretch units are arranged in a shape that is narrower in the crotch area of the wearer and broadens towards the front and rear waistline of wearer, the leg stretch units can be brought closer along the line of the body, and the leg stretch units are elongated and arranged favorably to fit around the legs of the wearer.

As described above, the separation distance D in the product widthwise direction W within the crotch region 25 between the leg stretch units 75 is smaller than the separation distances D within the front waistline region 20 and the rear waistline region 30 between the leg stretch units 75. Furthermore, the separation distance D within the rear waistline region 30 is greater than the separation distance D within the front waistline region 20.

Specifically, the interval (D1 in FIG. 1) between the inner ends of the leg stretch units 75 in the front waistline region 20 is narrower than the interval (D2 in FIG. 1) between the inner ends of the leg stretch units 75 in the rear waistline region 30.

That is, the leg stretch unit 75 provided in the rear waistline region 30 is positioned on the outer side in the product widthwise direction W of the leg stretch unit 75 provided in the front waistline region 20.

The interval is the distance between the inner ends of the leg stretch units 75 in the product widthwise direction W that is measured after expanding and holding the disposable diaper 10 from the natural state to the state when no wrinkles are formed, in the product longitudinal direction L and the product widthwise direction W.

As described above, owing to the synergistic effect with the fact of D2>D1, in a state where the fastening tape 90 is attached to the predetermined position of the target unit 95, the one end 75a of the leg stretch unit 75 is configured to be positioned between a base end 90a of the fastening tape 90 in the product widthwise direction W of the absorber 40 and an outer end 95a in the product widthwise direction W of the target unit 95. Furthermore, a part of the leg stretch units 75, having the smallest separation distance D overlaps with a narrow part of the absorbent core 40a (a part provided with the crotch stretch units 200) in the product longitudinal direction L.

The extension of the skin surface of the body of the wearer is particularly large in the hip, and is remarkable at a position towards the outer widthwise direction. Furthermore, the leg stretch units 75 are in contact with the body of the wearer. Because D2>D1, even when the movement of the wearer is transmitted to the disposable diaper 10, the leg stretch units 75 in the hip can extend while being in contact with the body, and even when the amount of change in the extension is large, the leg stretch units 75 do not become stiff. Therefore, the shifting of the disposable diaper 10 can be controlled by the leg stretch units 75.

Furthermore, the space between the legs of a wearer is smallest in the crotch region and expands from the crotch region towards the abdominal side or the dorsal side. Since the leg opening and the leg stretch unit 75 are shaped so as to extend outwardly in the widthwise direction as the leg opening and the leg stretch unit extend from the crotch region outwardly in the product longitudinal direction, the leg opening and the leg stretch unit 75 can be arranged along the leg of the wearer to prevent localized concentration of stress, which allows close contact with the wearer at a relatively low stretch rate, thereby making it possible to reduce the burden on the skin.

The leg stretch units 75 are configured to contract the disposable diaper by being bent along the legs of a wearer. Each of the ends in the product longitudinal direction of the leg stretch units 75 is arranged so as to expand in the widthwise direction and arranged in the vicinity of the waistline retaining unit. Therefore, each of the ends in the product longitudinal direction of the leg stretch units 75 acts so as to contract in the widthwise direction together with the waistline retaining unit.

Furthermore, in a case where a center line CT is set to a straight line which passes through a position having the smallest aforementioned separation distance D, that is, a position with the smallest interval between the pair of leg stretch units 75, and extends in parallel with the product widthwise direction W, a length L2 between the center line CT and the one end 75a positioned at the fastening tape 90 side of the leg stretch unit 75 is set to be greater than (L2>L1) or equal to (L2=L1) a length L1 between the center line CT and the other end 75b positioned at the target unit 95 side of the leg stretch unit 75. Furthermore, as the separation distance is set to be D2>D1, as described above, when the disposable diaper 10 is worn, the other end 75h of the leg stretch unit 75 crosses over the one end 75a of the leg stretch unit 75 at the abdominal side (the front waistline region 20 side) and projects towards the outer end 35a in the product longitudinal direction L of the leg opening 35, that is, towards the abdominal side. Thus, owing to the leg stretch units 75, the outer ends 35a in the product longitudinal direction L of the leg openings 35 to which the load in association with movement of a wearer is most likely to be applied can be prevented from shifting.

Specifically, in a case where the radius of curvature (R) of the outwardly-bending leg stretch unit 75 is compared between the dorsal side (the rear waistline region 30 side) and the abdominal side with respect to the center line CT of the leg stretch unit 75, the radius of curvature at the dorsal side is greater than that at the abdominal side. For example, the radius of curvature at the abdominal side may be 250 to 320 mm while the radius of curvature at the dorsal side may be 400 to 470 mm. Furthermore, the leg stretch unit 75 extending from the crotch region 25 towards the rear waistline region 30 is convex outwardly in the product widthwise direction while the leg stretch unit 75 extending from the crotch region 25 towards the front waistline region 20 is convex inwardly in the product widthwise direction.

Accordingly, the leg stretch unit 75 at a position corresponding to the dorsal side, that is, the buttocks of a wearer is more projected outwardly in the product widthwise direction W, so that the buttocks as a region having the swell of body can be widely covered and the leg stretch unit 75 can be projected to the outer end in the product longitudinal direction L of the leg opening 35 at the time of wearing of the disposable diaper 10. Thus, owing to the leg stretch units 75, the outer ends in the product longitudinal direction 14 of the leg openings 35 to which the load in association with movement of the wearer is most likely to be applied can be prevented from shifting.

(3) Shape of Crotch Stretch Unit

Next, the shape of the crotch stretch unit 200 will be described. As described above, the disposable diaper includes the crotch stretch unit 200. When the disposable diaper is worn, the crotch stretch unit 200 is configured to be easily maintained in a flat shape in a part of the crotch region compared to the other portions of the absorber 40 r. The crotch stretch unit 200 is configured to be stretchable at least in one of the product longitudinal direction L or the product widthwise direction W.

The crotch stretch unit 200 is provided separately and independently of the leg stretch units 75, and is configured to shrink by 60% or more of the length in the widthwise direction of the absorbent core 40a in the position where the crotch stretch unit overlaps the absorbent core 40a (in at least one embodiment, it is the position between the core wrap 40b that wraps the absorbent core 40a and the backsheet 60a). In this way, due to the shrinkage of the portion in which the absorbent core 40a is arranged with the crotch stretch unit 200, the absorbent core 40a is constricted, and a flat shape is easily maintained as compared to the portion where the absorbent core 40a is not constricted.

Furthermore, owing to the crotch stretch unit 200, the crotch region 25 follows the shape of the body, so that the disposable diaper 10 is less likely to shift. Although the crotch region 25 becomes heavier or the absorbent core 40a is thickened especially when the disposable diaper 10 absorbs excretions, even in such a case, the crotch region 25 of the disposable diaper 10 is more likely to follow the shape of the body owing to the crotch stretch unit 200, so that the shifting of the disposable diaper 10 can be prevented effectively.

On the other hand, the absorbent core 40a positioned in the front waistline region and the back waistline region located outwardly in the product longitudinal direction from the crotch stretch unit 200 is not shrunk by the crotch stretch unit 200, because of which the crotch stretch unit 200 that is maintained in a flat shape in crotch region 25 of the disposable diaper, when the disposable diaper is retained around the waistline and waist of the wearer by the fastening tapes, does not come excessively close to the body and is therefore arranged appropriately along the body.

Furthermore, when the crotch stretch unit 200 is stretchable along the product longitudinal direction L, the front waistline region 20 and the rear waistline region 30 rise up easily due to the shrinkage of the crotch stretch unit 200. When the disposable diaper is worn, a flat crotch region is formed along the body at the crotch of the wearer.

Because the front waistline region and the back waistline region rise up from the crotch stretch unit 200, the fitting of the disposable diaper 10 on the wearer improves.

That is, owing to the contraction of the crotch stretch unit 200, the disposable diaper 100 can be worn stably on a wearer so that the crotch region 25 of the disposable diaper 10 is arranged at the crotch of the wearer.

The crotch stretch unit 200 is preferably made from a stretch sheet.

A stretch sheet configures the crotch stretch unit 200, the absorbent core 40a in a region in which the stretch sheet is arranged is uniformly contracted, so that the flat shape can be maintained more easily. It is to be noted that as for a stretch sheet, the stretch sheet similar to that of the leg stretch unit 75 may be used.

Furthermore, instead of the stretchable sheet, the crotch stretch unit 200 can also be configured by arranging a plurality of thread-like or band-like elastic members made from polyurethane elastic fibers and natural rubber. In this case, in order to uniformly constrict the absorbent core 40a by the crotch stretch unit 200, the interval between the elastic members is preferably 7 mm or less, and more preferably 5 mm or less. Furthermore, in order to uniformly constrict the absorbent core 40a, the difference in the interval between adjacent elastic members is desired to be 2 mm or less.

Furthermore, the ratio of expansion and contraction of the crotch stretch unit 200 is preferably 1.2 times or more and 1.8 times or less, specifically. In at least one embodiment, the ratio of expansion and contraction of the crotch stretch unit 200 is set to 1.4 times. The ratio of expansion and contraction of the crotch stretch unit 200 implies the extent of the expansion and contraction of the crotch stretch unit 200 in the direction of expansion and contraction (product longitudinal direction 1), and is stipulated as below:

> The ratio of expansion and contraction of the crotch stretch unit 200=(Length of the crotch stretch unit 200 in the maximum stretched state)/(Length of the crotch stretch unit 200 in the natural state)

The ratio of expansion and contraction as used herein is to be measured as described below, for example.

Firstly, if the disposable diaper 10 is inserted in a package, for example, then the disposable diaper 10 is taken out of the package, and the diaper is kept in such a condition for 60 minutes in an atmosphere having a temperature of 20° C.±2° C., and a relative humidity of 60%±5% RH, and the length of the crotch stretch unit is measured along the stretching direction. This length is the "Length of the crotch stretch unit 200 in the stretching direction, in the natural state".

Secondly, the length in the stretching direction of the desired region of the open-type disposable diaper in this state (that is, in the natural state), and the length in the stretching direction of the desired region, when the open-type disposable diaper is extended from its natural state until wrinkles caused by the elastic members are not visible, are measured.

This length is the "Length of the crotch stretch unit 200 in the stretching direction, in the maximum stretched state".

The ratio of expansion and contraction is measured by using these measurement results and calculating according to the formulae described above.

By thus setting the ratio of expansion and contraction of the crotch stretch unit 200 between 1.2 times and 1.8 times, it is possible to favorably follow the stretching of the skin of the wearer.

For example, when the wearer bends forward such that the front side of the body constricts, there exists a part in the skin at the side of the hip portion of the wearer that stretches by approximately 30% as compared to the state when the body has been stretched out.

That is, when the ratio of expansion and contraction of the crotch stretch unit 200 is 1.2 times or less, the shrinkage of the crotch stretch unit 200 in the natural state of the disposable diaper may be insufficient, and as compared to the case when the crotch stretch unit 200 has not been provided, the shrinkage of the absorber region in the crotch of the disposable diaper 10 is small, and the disposable diaper may not be able to sufficiently take a flat shape in the crotch of the wearer so as to run along the body.

On the other hand, when the ratio of expansion and contraction of the crotch stretch unit 200 is more than 1.8 times, the contraction size in the contracting direction of the crotch stretch unit 200 may become too large, because of which the region where the crotch stretch unit 200 exists easily may come into close contact with the body of the wearer rather than running along it, and the disposable diaper 10 may easily shift to the lower side of the wearer.

Furthermore, the structure may be configured so that the amount of shrinkage in the product longitudinal direction L of the crotch stretch unit 200 is set to 2 to 8% of the length in the product longitudinal direction L of the disposable diaper 10, for example It is to be noted that the amount of shrinkage represents the difference between a length "b (mm)" of the sample in the stretched-out state where wrinkles are reduced in number so that the surface of the sample becomes almost smooth and the length "a (mm)" of the sample in the natural state oriented in the direction of expansion and contraction n of the sample, and the amount of shrinkage can be calculated by (b−a).

In the present specification, measurement of "length" is performed using a spring measure (a tape measure coated with fiberglass-reinforced vinyl chloride) manufactured by Shinwa Rules Co., Ltd., such that the measure is set along a portion to be measured.

The inventor(s) of the present invention confirmed that the crotch stretch unit 200 is likely to extend suitably along the body of a wearer during a process of putting the disposable diaper 10 on the wearer, in a case where the amount of shrinkage in the product longitudinal direction L of the crotch stretch unit 200 is set to 2 to 8% of the length in the product longitudinal direction L of the disposable diaper 10.

Herein, in a case of the amount of shrinkage in the product longitudinal direction L of the crotch stretch unit 200 being set greater than 8%, the crotch stretch unit 200 may shrink too much to keep sufficient length in the product longitudinal direction L of the disposable diaper 10, thereby making it difficult to put the disposable diaper 10 onto the body of a wearer or making it easy to cause shifting due to too tight contact between the disposable diaper 10 and the body of the wearer in the crotch region 25.

On the other hand, in a case of the amount of shrinkage in the product longitudinal direction L of the crotch stretch unit 200 being smaller than 2%, the crotch stretch unit 200 may be less likely to produce the effect to bring the disposable diaper 10 close to the body of a wearer.

Furthermore, the center 200x of the crotch stretch unit 200 in the product longitudinal direction L is arranged at the side of the front waistline region 20 from the center 10x of the disposable diaper 10 in the product longitudinal direction L However, the crotch stretch unit 200 is arranged to run across (i.e., overlap) the center of the disposable diaper 10 in the product longitudinal direction L.

In such a case, in view of the rigidity of the absorbent core 40a and the rigidity of other members configuring the disposable diaper 10, the thickness of the elastic members configuring the crotch stretch unit 200 and the arrangement pitch of the elastic members can be selected appropriately, however, when the main body of the disposable diaper 10 is in the natural state (unexpanded state), the entire side edge in the product widthwise direction W of the absorbent core 40a is preferably in a contracted state.

In addition to the fact that the load on the outer end in the product longitudinal direction L of the leg opening 35 at the time of wearing the disposable diaper 10 is reduced owing to the structure of the leg stretch unit 75 as described above, the load on the outer end in the product longitudinal direction L of the disposable diaper 10 at the time of wearing is reduced owing to the crotch stretch unit 200 making the crotch unit of the absorbent core 40a to follow the shape of the body, which further eases up the situation where the load is applied to the fastening tape 90 due to movement of a wearer. This prevents effectively the disposable diaper 10, especially the vicinity of the leg openings 35 from shifting.

Furthermore, a notch 115 (notch 125) is formed in the crotch region of the absorber 40. The notch 115 and the notch 125 correspond to a region in which the absorbent core 40a configuring the absorber 40 does not exist. In at least one embodiment, the notch 115 and the notch 125 correspond to a low rigidity unit in which the basis weight of the absorbent core 40a is lower than that of the other portion of the absorbent core 40a. Instead of forming the notch 115 and the notch 125, the region of the notch 115 and the notch 125 may be such that the basis weight of the absorbent core 40a is lower than that of the other portion of the absorbent core 40a.

The notch 115 and the notch 125 exist along the edges in the product longitudinal direction L of the crotch stretch unit 200. Even though the notch 115 and the notch 125 are formed, the absorbent core 40a positioned in the front waistline region 20 and the rear waistline region 30, and the absorbent core 40a positioned in the crotch region 25 are preferably in continuation, particularly in the widthwise direction, rather than being completely separate.

As the notch 115 and the notch 125 run outwardly in the product widthwise direction W, the length of the notch 115 and the notch 125 in the product longitudinal direction L keeps on widening. As a result of such a shape, the outer side in the product widthwise direction W of the absorbent core 40a is constricted more easily, and a flat "bottom unit" is formed more easily. Furthermore, the absorbent core 40a positioned towards the front waistline region 20 from the notch 115, and the absorbent core 40a positioned towards the rear waistline region 30 from the notch 125 rise up from the "bottom unit", and can easily curve along the roundness of the body of the wearer (the abdominal portion and the hip), because of which the shape of the disposable diaper can be brought closer to the body of the wearer.

Furthermore, the edge towards the front waistline region 20 (rear waistline region 30) of the notch 115 (notch 125) may be arc shaped. The shape of the edge of the notch 115 (notch 125) is such that the center of the arc is positioned in the rear waistline region 30 (front waistline region 20) from the edge. As a result of such a shape, the deformation along the roundness of the body of the wearer occurs more easily and remarkably.

(4) Method of Manufacturing the Disposable Diaper

Next, an example of the method of manufacturing the disposable diaper according to at least one embodiment will be described. For processes not described herein, existing processes can be used. Furthermore, the manufacturing method explained below is only an example, and the disposable diaper can also be manufactured by other manufacturing methods. The method of manufacturing the disposable diaper includes at least a component forming step, a component loading step, a leg hole forming step, and a cutting step.

In the component forming step, the components configuring the disposable diaper are formed. Specifically, for example, an absorbent material is laminated and the absorber 40 is molded.

In the component loading step, components the configuring the disposable diaper 10, such as the stretch sheet configuring the leg stretch unit 75, other web such as a web configuring the topsheet, a leakage-preventing sheet, an absorber, and the like, are loaded on a web configuring the backsheet.

Specifically, the stretch sheet configuring the leg stretch unit 75 is stretched out and further transferred onto an intermittent drum while being displaced in the widthwise direction, and thereafter the stretch sheet is cut into an individual product length on the intermittent drum. The stretch sheets are interspaced at intervals in association with rotation of the intermittent drum and transferred onto the continuous web. In this manner, the leg stretch unit can be arranged in a curved line.

In the leg opening forming step, the topsheet 50, the exterior sheet 60, and the backsheet 60*a* are cut along the widthwise outer end of the leg stretch unit 75. In this manner, the leg openings 35 arranged around the legs of a wearer are formed.

In the cutting step, the continuous body on which the topsheet 50, the backsheet 60*a*, and the absorber 40 are arranged is cut in the size of one product along the product widthwise direction W. The disposable diaper 10 is thus manufactured.

(5) Operation and Effect

FIG. 4 is a view for showing a state in which the disposable diaper 10 according to at least one embodiment of the present invention is worn by a wearer (an infant or toddler). As described above, in the disposable diaper 10, when the fastening tapes 90 are attached into the target units 95 in the front waistline region 20, a part of the side flaps 70 in the rear waistline region 30 is superimposed on the front waistline region 20. The rear waistline region 30 crosses over the side abdominal area of a wearer to reach up to a position closer to the abdominal side and gets attached into the target units 95.

Since the legs of a wearer stick out not from the sides of the body but from the waistline area closer to the abdominal area than the sides of the body, it is preferable that the leg holes be formed at a position a little closer to the front than the sides and elastic members be placed annularly along the leg hole regions having a cross section in a circular shape. In at least one embodiment, the leg stretch unit 75 has a part bending outwardly in the product widthwise direction W as the leg stretch unit 75 extends from the crotch region 25 outwardly in the product longitudinal direction L, and the leg stretch unit 75 extending from the crotch region 25 towards the rear waistline region 30 is convex outwardly in the product widthwise direction W while the leg stretch unit 75 extending from the crotch region 25 towards the front waistline region 20 is convex inwardly in the product widthwise direction W. Furthermore, the leg stretch unit 75 extending from the crotch region 25 towards the rear waistline region 30 is convex outwardly in the product widthwise direction while the leg stretch unit 75 extending from the crotch region 25 towards the front waistline region 20 is convex inwardly in the product widthwise direction. FIG. 1 shows a part 751 in a convex form towards the outer side in the widthwise direction of the leg stretch unit 75 and a part 752 in a convex form towards the inner side in the widthwise direction of the leg stretch unit 75.

Therefore, a line formed by the disposable diaper 10, extending from the buttocks of a wearer to the crotch of the wearer and the inguina of the wearer, is formed in a shape suitable for the leg holes positioned a closer to the front than the sides. Therefore, the leg openings 35 are open towards the abdominal side at the time of attaching the fastening tapes 90 to the target units 95, so that the shape becomes more suitable for the body shape.

Furthermore, the separation distance D2 within the rear waistline region 30 is greater than the separation distance D1 within the front waistline region 20. Therefore, the leg stretch unit 75 bending and extending from the crotch region 25 has the one end 75*a* covered with the other end 75*b* when the fastening tape 90 is attached to the target unit 95, thereby extending up to a position closer to the abdominal side of a wearer.

As a result, the shape is made more suitable for the body shape even in a case where a wearer makes leg movements, especially where the wearer takes a posture (a sitting posture) to bend their body, which causes the skin of area from the top of buttocks to the base of thighs to stretched out and the front waistline region 20 of the disposable diaper 10 to come in tight contact with the swell of abdomen. Therefore, no sheets making up the disposable diaper 10 get projected, thereby making it less likely to cause the shifting.

Further, in a state where the fastening tape 90 is attached to the predetermined position of the target unit 95, the one end 75*a* in the product longitudinal direction L of the leg stretch unit 75 is superimposed on the other end 75*b* of the leg stretch unit 75. Therefore, when the disposable diaper 10 is worn by an infant or toddler, each of the leg stretch units 75 forms a circular stretch unit surrounding the entire periphery of each of the legs of the wearer. Furthermore, the one end 75*a* and the other end 75*b* of the leg stretch unit 75 come in close contact with each other by the fastening tape 90 being attached to the target unit 95, thereby forming the strong circular stretch unit which is hardly released. Therefore, the leg stretch units 75 forming a circular shape fit along the legs of a wearer, so that the disposable diaper 10 is less likely to shift downward of the body of the wearer even in a case where the wearer takes a posture (a sitting posture) to bend their body.

Furthermore, in at least one embodiment, the length L2 between the center line CT and the one end 75*a* positioned at the fastening tape 90 side of the leg stretch unit 75 is greater than the length L1 between the center line CT and the other end 75*b* positioned at the target unit 95 side of the leg stretch unit 75. The leg opening 35 is curved because it is convex inwardly in the product widthwise direction W of the absorber 40, and owing to the leg stretch units 75 curved in this manner and the fact of L2>L1, the leg stretch units 75 are arranged along the round legs of a wearer. Furthermore, as described above, since the separation distance is set to be D2>D1, the leg stretch unit 75 can prevent the shifting of the outer end in the product longitudinal direction L of the leg opening 35 to which the load in association with movement of the wearer is most likely to be applied.

Furthermore, since the leg stretch unit 75 projecting manner outwardly in the longitudinal direction L from the target unit 95, the leg stretch unit 75 at the target unit 95 side is superimposed on the side flap 70 and/or the leg stretch unit 75 at the fastening tape 90 side is superimposed on the side flap 70, thereby coming in close contact with the entire region of the leg of a wearer. Furthermore, owing to the fact of L2>L1, the leg stretch unit 75 at the target unit 95 side is covered so as to cover the circumference of buttocks with the swell, and thus the leg stretch unit 75 can come in close contact with the entire region of the leg of the wearer. Therefore, it is possible to counteract the force exerted to shift the disposable diaper 10 downward, so that the disposable diaper 10 can be supported by the leg stretch units 75 and peripheral of the leg stretch units 75 f.

In at least one embodiment, in a state where the fastening tape 90 is attached to the predetermined position of the target unit 95, the region of the side flap 70 having the presence of the fastening tape 90, the leg stretch unit 75, and the target unit 95 are arranged separately from each other. Therefore, although the disposable diaper 10 is less likely to shift downward of the body of a wearer, if the leg stretch unit 75 is superimposed on the region of the side flap 70 having the presence of the fastening tape 90 or the target unit 95, contraction occurs in the longitudinal direction within the superimposed region, thereby making it more likely to cause the shifting in these elements for retaining the body in the circumferential direction, which is undesirable.

In at least one embodiment, a width W1 of the side flap 70 in the front waistline region 20 is smaller than a width W2 of the side flap 70 in the rear waistline region 30. This makes it easier to form the leg holes at the position a little closer to the front than the aforementioned sides.

(6) Other Embodiments

As described above, although several embodiments are disclosed, it should not be interpreted that the statements and drawings of the present disclosure limit the present invention. From this disclosure, a variety of alternate embodiments, examples, and applicable techniques will become apparent to one ordinarily skilled in the art.

For example, in at least one of the above-described embodiments, the leg stretch unit 75 provided in the rear waistline region 30 is positioned at the outer side in the product widthwise direction W of the leg stretch unit 75 provided in the front waistline region 20. However, such a structure is not necessarily required. Furthermore, in at least one of the above-described embodiments, the separation distance D in the product widthwise direction W between the leg stretch units 75 becomes longer as the leg stretch units extend outwardly in the product longitudinal direction L. However, the separation distance D does not necessarily have to change in this way.

Furthermore, in a state where the fastening tape 90 is attached to the predetermined position of the target unit 95, the region of the side flap 70 having the presence of the fastening tape 90, the leg stretch unit 75, and the target unit 95 may not be arranged separately from each other. Furthermore, in at least one of the above-described embodiments, the length L2 between the center line CT and the one end 75a positioned at the fastening tape 90 side of the leg stretch unit 75 is greater than the length L1 (L2>L1) between the center line CT and the other end 75b positioned at the target unit 95 side of the leg stretch unit 75. However, such a shape is not necessarily required.

As described above, it is of course the case that the present invention includes various embodiments and the like not described here. Therefore, the technical range of the present invention is to be defined only by the inventive specific matter according to the adequate claims from the above description.

The entire contents of Japanese Patent Application No. 2012-218716 (filed on Sep. 28, 2012) are incorporated in the present specification by reference.

INDUSTRIAL APPLICABILITY

It is possible to provide a disposable diaper that is less likely to shift even when a wearer (an infant and toddler) takes a posture to bend their body.

The present invention may be summarized as follows:

A disposable diaper comprising:
a front waistline region;
a rear waistline region;
a crotch region;
a product longitudinal direction from the front waistline region towards the rear waistline region;
a product widthwise direction that is perpendicular to the product longitudinal direction;
an absorber including an absorbent core with a liquid retention property;
a pair of side flaps provided at side edges of the absorber in the product widthwise direction;
a fastening tape provided to each of the side flaps, projecting from the rear waistline region outwardly in the product widthwise direction, and configured to be attached to a target unit formed in the front waistline region;
a pair of leg openings provided in the side flaps, and concave inwardly in the product widthwise direction; and
a pair of leg stretch units expansible and contractible along the leg openings; wherein
each of the leg stretch units has a part bending outwardly in the product widthwise direction as the leg stretch unit extends from the crotch region outwardly in the product longitudinal direction;
a separation distance between the leg stretch units in the product widthwise direction in the crotch region is smaller than separation distances between the leg stretch units in the product widthwise direction in the front waistline region and the rear waistline region;
the separation distance in the rear waistline region is longer than the separation distance in the front waistline region;
the leg stretch units extending from the crotch region towards the rear waistline region are convex outwardly in the product widthwise direction; and
the leg stretch units extending from the crotch region towards the front waistline region are arranged in a convex form towards an inner side in the product widthwise direction.

The disposable diaper may include any one or more of the following features:

In a state where the fastening tape is attached to a predetermined position of the target unit, one end in the product longitudinal direction of the leg stretch unit is superimposed on the other end in the product longitudinal direction of the leg stretch unit.

In a state where the fastening tape is attached to a predetermined position of the target unit, one end in the product longitudinal direction of the leg stretch unit is positioned between a base end of the fastening tape in the product widthwise direction and an outer end in the product widthwise direction of the target unit; and a length between (i) a center line that passes through a position having the smallest separation distance and extends in parallel with the product widthwise direction, and (ii) one end positioned at a fastening tape side of the leg stretch unit is greater than a length between (a) the center line and (b) the other end positioned at a target unit side of the leg stretch unit.

In a state where the fastening tape is attached to the predetermined position, the region of the side flap having presence of the fastening tape, the leg stretch unit, and the target unit, are arranged separately from each other.

The absorbent core positioned in the crotch region has a narrow part having a smaller width in the product widthwise direction than that of the absorbent core positioned in the front waistline region and the rear waistline region; and the part of the leg stretch units having the smallest separation distance between the leg stretch units is superimposed on the narrow part in the product longitudinal direction.

The leg stretch units are made from a stretch sheet; and the width in the product widthwise direction of the leg stretch units in the crotch region is 5 mm or more and 45 mm or less, in a natural state of the disposable diaper.

The width of the side flap in the front waistline region is smaller than the width of the side flap in the rear waistline region.

A crotch stretch unit that is provided in the crotch region and expansible and contractible at least in one of the product longitudinal direction or the product widthwise direction, wherein the crotch stretch unit is provided independently of the leg stretch units and is superimposed on the absorbent core as seen in a plan view of the disposable diaper.

REFERENCE SIGNS LIST

10 . . . disposable diaper
20 . . . Front waistline region
25 . . . Crotch region
30 . . . Rear waistline region
35 . . . Leg openings
40 . . . Absorber
40a . . . Absorbent core
40b . . . Core wrap
50 . . . Topsheet
60 . . . Exterior sheet
60a . . . Backsheet
70 . . . Side flaps
71 . . . Elastic member
75 . . . Leg stretch unit
75a . . . one end
75b . . . other end
751 . . . widthwise inner end region
80 . . . Leg side gathers
81 . . . Joining portion
81A . . . First joining portion
81B . . . Second joining portion
82 . . . Free end portion
84 . . . contracting unit
85 . . . waistline stretch unit
90 . . . Fastening tape
91 . . . Base sheet
92 . . . Hook sheet
95 . . . Target unit
110 . . . Notch
115 . . . Notch
125 . . . Notch
200 . . . Crotch stretch unit

The invention claimed is:

1. A disposable diaper, comprising:
a front waistline region;
a rear waistline region;
a crotch region;
a product longitudinal direction from the front waistline region towards the rear waistline region;
a product widthwise direction that is perpendicular to the product longitudinal direction;
an absorber including an absorbent core with a liquid retention property;
a pair of side flaps provided at side edges of the absorber in the product widthwise direction;
a fastening tape provided to each of the side flaps, projecting from the rear waistline region outwardly in the product widthwise direction, and configured to be attached to a target unit formed in the front waistline region,
a pair of leg openings provided in the side flaps, and concave inwardly in the product widthwise direction;
a pair of leg stretch units expansible and contractible along the leg openings; and
a pair of elastic members provided at the pair of side flaps, respectively, to define leg side gathers extending in the product longitudinal direction,
wherein
the pair of elastic members is located between the pair of leg stretch units in the product widthwise direction,
each of the leg stretch units has a part bending outwardly in the product widthwise direction as the leg stretch unit extends from the crotch region outwardly in the product longitudinal direction;
a separation distance between the leg stretch units in the product widthwise direction in the crotch region is smaller than separation distances between the leg stretch units in the product widthwise direction in the front waistline region and the rear waistline region;
the separation distance in the rear waistline region is longer than the separation distance in the front waistline region;
the leg stretch units extending from the crotch region towards the rear waistline region are convex outwardly in the product widthwise direction; and
the leg stretch units extending from the crotch region towards the front waistline region are convex inwardly in the product widthwise direction.

2. The disposable diaper according to claim 1, wherein each of the leg stretch units has first and second ends opposing each other in the product longitudinal direction, and
in a state where the fastening tape is attached to a predetermined position of the target unit, the first end of the leg stretch unit is superimposed on the second end of the leg stretch unit in a product thickness direction of the disposable diaper.

3. The disposable diaper according to claim 1, wherein each of the leg stretch units has a first end positioned at a fastening tape side and a second end positioned at a target unit side, said first and second ends opposing each other in the product longitudinal direction,
in a state where the fastening tape is attached to a predetermined position of the target unit, one of the first and second ends of the leg stretch unit is positioned between a base end of the fastening tape in the product widthwise direction and an outer end of the target unit in the product widthwise direction, and
a length between (i) a center line that passes through a position having the smallest separation distance and extends in parallel with the product widthwise direction, and (ii) the first end of the leg stretch unit is greater than a length between (a) the center line and (b) the second end of the leg stretch unit.

4. The disposable diaper according to claim 2, wherein in the state where the fastening tape is attached to the predetermined position, a region of the side flap having the fastening tape, the leg stretch unit, and the target unit are arranged separately from each other.

5. The disposable diaper according to claim 1, wherein
the absorbent core positioned in the crotch region has a narrow part having a smaller width in the product widthwise direction than that of the absorbent core positioned in the front waistline region and the rear waistline region; and
a part of the leg stretch units having the smallest separation distance between the leg stretch units is superimposed on the narrow part in the product longitudinal direction.

6. The disposable diaper according to claim 1, wherein each of the leg stretch units is a stretch sheet; and
the width in the product widthwise direction of each of the leg stretch units in the crotch region is 5 mm or more and 45 mm or less in a natural state of the disposable diaper.

7. The disposable diaper according to claim 1, wherein the width of each of the side flaps in the front waistline region is smaller than the width of the side flap in the rear waistline region.

8. The disposable diaper according to claim 1, further comprising:
a crotch stretch unit that is provided in the crotch region and expansible and contractible at least in one of the product longitudinal direction or the product widthwise direction,
wherein the crotch stretch unit is provided independently of the leg stretch units and is superimposed on the absorbent core as seen in a plan view of the disposable diaper.

9. The disposable diaper according to claim 1, further comprising:
a liquid-permeable topsheet; and
a liquid-impermeable backsheet,
wherein
the pair of side flaps is directly attached to the liquid-permeable topsheet, and
the pair of leg stretch units is directly fixed between the pair of side flaps and the liquid-impermeable backsheet.

* * * * *